United States Patent
Pretorius et al.

(10) Patent No.: US 10,048,484 B2
(45) Date of Patent: Aug. 14, 2018

(54) IMAGING SYSTEM AND IMAGING METHOD

(75) Inventors: Marco Pretorius, Oberkochen (DE);
Markus Seesselberg, Aalen (DE);
Artur Hoegele, Oberkochen (DE);
Christoph Nieten, Jena (DE); Enrico Geissler, Jena (DE)

(73) Assignees: Carl Zeiss AG, Oberkochen (DE); Carl Zeiss Meditec AG, Jena (DE)

( * ) Notice: Subject to any disclaimer, the term of this patent is extended or adjusted under 35 U.S.C. 154(b) by 527 days.

(21) Appl. No.: 13/977,683

(22) PCT Filed: Dec. 21, 2011

(86) PCT No.: PCT/EP2011/073584
§ 371 (c)(1),
(2), (4) Date: Oct. 25, 2013

(87) PCT Pub. No.: WO2012/089581
PCT Pub. Date: Jul. 5, 2012

(65) Prior Publication Data
US 2014/0049633 A1 Feb. 20, 2014

(30) Foreign Application Priority Data
Dec. 30, 2010 (DE) .................. 10 2010 064 387

(51) Int. Cl.
*G02B 21/36* (2006.01)
*G02B 21/00* (2006.01)
*G02B 21/22* (2006.01)
*G02B 27/00* (2006.01)
*A61B 3/13* (2006.01)

(52) U.S. Cl.
CPC .............. *G02B 21/365* (2013.01); *A61B 3/13* (2013.01); *A61B 3/132* (2013.01); *G02B 21/0012* (2013.01); *G02B 21/22* (2013.01); *G02B 27/0075* (2013.01); *G02B 21/367* (2013.01)

(58) Field of Classification Search
CPC ................ G02B 21/22; G02B 21/0012; H04N 13/0242; A61B 3/13
See application file for complete search history.

(56) References Cited

U.S. PATENT DOCUMENTS

| 3,305,294 A | 2/1967 | Alvarez |
| 4,925,281 A | 5/1990 | Baker |

(Continued)

FOREIGN PATENT DOCUMENTS

| DE | 1 029 591 B | 5/1958 |
| DE | 1 803 964 A1 | 6/1969 |
| WO | 2007037691 A2 | 4/2007 |

OTHER PUBLICATIONS

English language translation of International Preliminary Report on Patentability for PCT/EP2011/073584, Jul. 11, 2013, 15 pages.

(Continued)

*Primary Examiner* — Zhubing Ren
(74) *Attorney, Agent, or Firm* — Skaar Ulbrich Macari, P.A.

(57) ABSTRACT

An imaging system with an imaging lens system for imaging an object into an image plane is disclosed. The imaging lens system contains an optical component for a higher depth of field, of which the refractive power is alterable and the optical effect remains rotation-symmetrical.

25 Claims, 7 Drawing Sheets

(56) References Cited

U.S. PATENT DOCUMENTS

| | | |
|---|---|---|
| 5,880,711 A | 3/1999 | Tamada |
| 5,896,223 A | 4/1999 | Tigliev et al. |
| 7,444,014 B2 | 10/2008 | Dresser et al. |
| 7,704,206 B2 * | 4/2010 | Suzuki .................. A61B 1/043 348/70 |
| 2004/0228005 A1 | 11/2004 | Dowski et al. |
| 2006/0181767 A1 | 8/2006 | Hanzawa |
| 2006/0256429 A1 | 11/2006 | Obrebski et al. |
| 2007/0047094 A1 | 3/2007 | Winterot et al. |
| 2008/0214940 A1 * | 9/2008 | Benaron et al. .............. 600/478 |

OTHER PUBLICATIONS

Tucker S.C. et al.: "Extended depth of field and aberration control for inexpensive digital microscope systems", Optics Express, OSA, Washington DC (US), vol. 4, No. 11, Jan. 1, 1999, pp. 1-8.

* cited by examiner

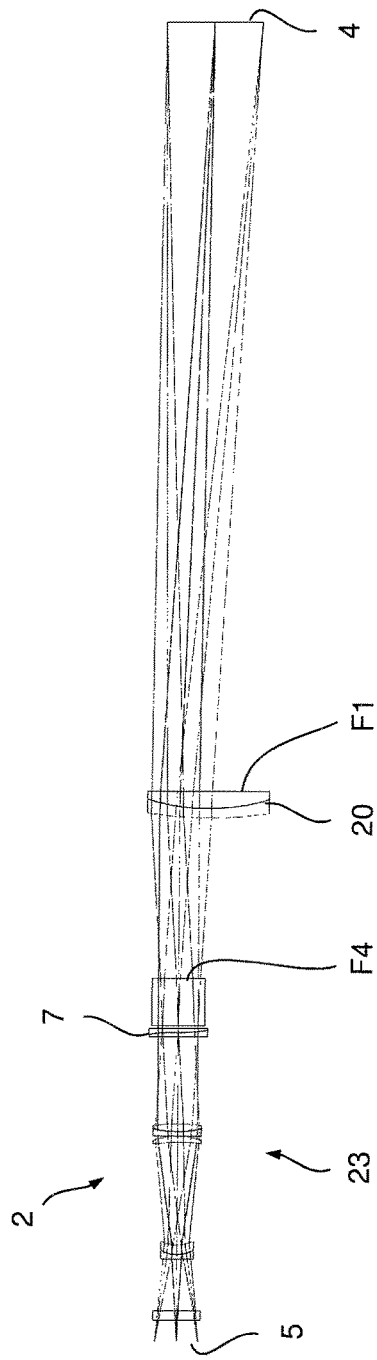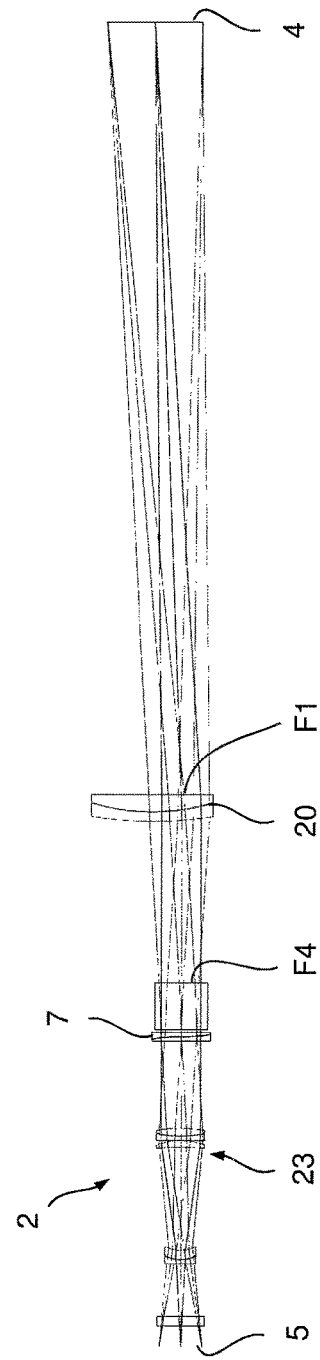

IMAGING SYSTEM AND IMAGING METHOD

PRIORITY

This application claims the benefit of International Application PCT/EP2011/073584 filed on Dec. 21, 2011, and German Patent Application No. 102010064387.4, filed on Dec. 30, 2010, both of which are hereby incorporated herein by reference in their entirety.

FIELD

The present invention relates to an imaging system and an imaging method, such as e.g. a microscope and a microscopy method.

With such an imaging system and such an imaging method, there is the need for an increase in the depth of field.

BACKGROUND

It has long been known that a complete digitization of the imaging chain in microscopy would make a whole range of fundamental advantages possible. Thus, for example, very light-sensitive cameras could help to lower the necessary illumination level on the object of observation and thus reduce the thermal load. Very fast cameras can record movements or variable processes which cannot be resolved with direct visual observation. Cameras with a broad spectral band can expand the perceptible wavelength range into infrared or near-ultraviolet in order for example to make fluorescence of dyes or luminescence of particular marker substances visible. Furthermore, the number of observers could in principle be made as large as desired.

At the same time, the user increasingly expects image data to be able to be easily archived. In the case of surgical microscopes, for instance, this is also for the purpose of meeting obligations to provide proof of quality and for teaching purposes. In respect of the image representation itself, users increasingly expect images to be presented to them that are ergonomically adapted optimally to their aesthesiophysiology, for instance by targeted adaptation of contrast or colour space, or by applying suitable noise suppression or image sharpening algorithms, etc., such as is already common practice in digital consumer products (for instance HDTVs, digital photography, etc.).

A problem not solved sufficiently until now which increasingly occurs with digital image acquisition devices is that the depth of field in the object space is in principle coupled to the lateral resolution and tends to be too low for many fields of application. In the at least approximately diffraction-limited case, the object-side lateral resolution (minimum resolvable structure width) is proportional to $\lambda/NA$ and the object-side longitudinal resolution (=depth of field) is proportional to $\lambda/NA^2$, wherein $\lambda$ is the wavelength of the light used for observation and NA is the object-side numerical aperture of the optical system.

Thus while the resolution of smaller structures requires an enlargement of the object-side numerical aperture, on the other hand the depth-of-field range in the object area is thereby strongly disproportionately reduced, namely according to a quadratic law. In devices for direct visual observation, this is mitigated by the fact that, when focusing on particular objects as carriers of image information, the eye of an observer unconsciously (by reflex) accommodates to the observed depth level in which the maximum object contrast lies. However, this accommodation no longer takes place with the digital acquisition and representation of image information, which is why the depth of field of the images presented on a display is too low for many applications.

This fundamental disadvantage has until now prevented digital microscope systems from comprehensively conquering particular fields of use in which a sufficient depth of field is crucial. This is the case for example when small objects are manipulated under constant microscopic observation. An important example of this is microscope-assisted surgery, for example ophthalmic, dental, neuro- or spinal surgery in which a sufficient depth of field is absolutely essential.

To increase the depth of field in digital image acquisition devices, various methods are already known which can be roughly distinguished according to static and dynamic methods.

A device for increasing the depth of field is known from DE 1 803 964 in which a rotating optical element is divided into sectors which are to have a different optical refractive power effect. These are introduced into the beam path periodically by rotating the element.

However, a disadvantage of this operating principle is that a rotary device for refocusing only functions for discrete z-positions, and thus corresponding discrete angular positions of the rotatable element. A continuous movement of the element would always lead to a blurriness in the imaging because a rotation-symmetrical pupil manipulation is only possible when the optical axis of the microscope and the optical axis of the optical element are located in one line of sight on the rotatable device. In all other angular positions, however, the rotatable element will induce non-rotation-symmetrical imaging errors which are not acceptable for high-quality imaging. It is therefore necessary to rotate the rotatable disc in each case by discrete angular positions, thus to accelerate it in the interim, decelerate it again and then record a partial image. In practice, this substantially limits the usable video frame rate.

In addition, the diameter of the disc is necessarily several times greater than the diameter of the microscope lens system, resulting in a bulky component which would also produce a relatively high level of disruptive mechanical vibrations as a result of the necessary acceleration and deceleration. Furthermore, only relatively few discrete z-positions of the focal position, which are also not freely adjustable, can be realized with such an element.

In DE 10 2006 025 129 A1, an arrangement is described in which a micromirror array with individually controllable micromirrors with adjustable spatial orientation is to be used to alter the focal plane. However, there are no specific embodiment examples in the published document.

A variable mirror with optical refractive power which deflects the beam path by 45° would produce strongly non-rotation-symmetrical image errors which vary with the switching state of the mirror and therefore also cannot be corrected by static optical elements. In addition, a segmentation of the pupil, which in principle cannot be avoided due to the mirror microfacets, would produce light interference which is superimposed on the useful light beam path and cannot be separated from it. Furthermore, the required micromirror matrix is an expensive and complex specialized component which is not yet available as a commercial product. Finally, with this operating principle, at least one fold of the beam path is necessary, which in general is not desired in surgical microscopes for design reasons. Here, the visual axis is to coincide as much as possible with the mechanical axis of the device, in order that a precise positioning of the video head that is as intuitive as possible for the operator is more easily possible.

Furthermore, lenses or lens groups can be shifted mechanically to adjust the focal position in the longitudinal direction, as described e.g. in US 2006/0181767 A1. A disadvantage of this is that to achieve a predetermined alteration range of the focal plane relatively large displacement paths are necessary, which cannot, or can only with difficulty, be realized mechanically in the desired frequency. Moreover, relatively large shocks and vibrations are induced which are to be seen as problematic with respect to both the positional tolerance requirements of the optical elements and the purely acoustic interference effect.

The static methods include the use of special phase- and amplitude-modulating masks in the area of the pupil of an optical system (so-called EDOF masks). By means of such methods (known under the name "PSF engineering") the linear expansion of the central diffraction maximum of the point spread function of the optical system can be enlarged and thus the optical depth of field can be increased. On the other hand, with known PSF an image reconstruction in other z-planes can take place, by unfolding operations within certain limits, as described e.g. in U.S. Pat. No. 7,444,014 B2.

However, a disadvantage here is that such phase masks always also reduce the image contrast (which can be quantified more precisely for example by the modulation transfer function) compared with a diffraction-limited system with an identical aperture but without phase mask. In particular, the best achievable resolution within a particular plane can be made significantly worse, which is not acceptable for many applications.

Furthermore, amplitude masks absorb a certain portion of the light used for the imaging. This is also problematic in many applications, wherein a compensation for the transmission losses by a higher illumination level is often not acceptable because of the associated higher radiation and thermal load, such as e.g. in the case of ophthalmological applications. Furthermore, it is disadvantageous that, as the depth of field increases, the noise of the image sensor leads to ever greater impairment of the quality of the reconstructed image.

SUMMARY

Starting from here, the object of the invention is therefore to provide an imaging system with increased depth of field, as well as a corresponding imaging method.

The object is achieved by an imaging system with an imaging lens system for imaging an object into an image plane, wherein the imaging lens system contains an optical component for a higher depth of field, of which the refractive power is alterable and the optical effect remains rotation-symmetrical.

Through the alterable refractive power the focal length and back focal length of the imaging lens system can be altered, and thus an alteration of the focal position in the direction of the optical axis can be carried out. Since the optical effect of the optical component remains rotation-symmetrical, images with excellent image quality are still possible, with the result that images with varying depth of field are possible. In particular, these variations can be carried out very quickly and/or continuously, with the result that e.g. an observer who can perceive the image in the image plane has a visual impression with increased depth of field.

The imaging system can have an image acquisition unit which records the image of the object with different refractive power values of the optical component (and thus with different focal positions) in the image plane and conveys it to an image processing unit, wherein, using the pictures, the image processing unit produces a complete image of the object with higher depth of field compared with one of the pictures.

The thus-produced complete image can then be presented to a user e.g. via a display unit. The complete image can be presented for example as a live image.

The imaging system can have a control module for the optical component which brings about a desired alteration of the refractive power. The control module can be a constituent of a control unit of the imaging system.

The display unit can effect a two-dimensional or also, preferably, a three-dimensional representation. All known display methods and devices are possible. In particular, the display unit can be an autostereoscopic display unit. However, it is also possible for the user to have to wear corresponding glasses (for example shutter glasses) to receive the three-dimensional visual impression. Furthermore, the display unit can also be formed as a so-called HMD unit. In this case, the user wears glasses and a separate image is presented to each of the user's eyes. In this manner, an excellent 3D representation with increased depth of field is also possible.

In the imaging system, the refractive power of the optical component can be continuously alterable. In particular, the imaging system can also have an actuator which effects the alteration of refractive power.

The alteration of refractive power can preferably be a periodic alteration of refractive power.

The optical component can be for example a deformable lens. For example, an elastomer lens can be provided in which the curvature of an outer surface or of a boundary surface between two chambers with media of different refractive indices is altered by means of an application of pressure. The optical component can also be formed as a liquid lens in which a contact angle is altered by means of electrical voltage and a spherical boundary surface between two liquids of different refractive indices is produced.

Preferably, the optical component has two refractive elements which each have at least one free-form surface, wherein the two elements can be shifted relative to each other transverse to the optical axis of the imaging lens system in order to thereby effect the desired alteration of refractive power. The optical component can also have more than two refractive elements.

The two free-form surfaces can be formed in particular such that they behave exactly mirror-symmetrical to each other in a zero position. If the other sides of the elements are each formed as flat sides, the two elements in the zero position are almost a coplanar plate.

The free-form surfaces are in particular surfaces which can be described by the following third-order polynomial:

$$z(x, y) = k_1 \cdot \left(x^2 \cdot y + \frac{y^3}{3}\right) + k_2 \cdot y$$

wherein it is assumed here that the lateral shift of the elements takes place along the y-axis. The polynomial describing the free-form surface can also contain even higher orders which can then be used to correct errors of the imaging lens system.

By varying k1, the alteration of refractive power per displacement path is generally predetermined. By varying $k_2$, a tilt (rotation about the x-axis) of the free-form surface is additionally set which can be used, in the case of a given profile shape, to minimize the average thickness of the element (which follows from the requirement that, to ensure a sufficient stability, the glass thickness must not, at any point of the optically used area, fall below a particular minimum value) and thus the mass of the element.

For simplification, $k_2=0$ can be set, with the result that the following formula arises:

$$z(x, y) = k \cdot \left(x^2 \cdot y + \frac{y^3}{3}\right)$$

However, it has been shown that the additional term with $k_2 \neq 0$ is often advantageous.

Furthermore, by free-form surface is meant here in particular a curved surface which is formed, however, neither spherically curved nor rotation-symmetrical. In particular, it has no or at most one mirror symmetry plane.

By the rotation-symmetrical optical effect of the optical component is meant here in particular that the optical component is formed such that its optical effect is as precisely rotation-symmetrical as possible. If the optical component is formed e.g. from the two refractive elements, even with ideally accurate production, non-rotation-symmetrical residual errors can occur which are, however, so small that the optical effect can still be described as rotation-symmetrical.

The refractive elements can have a thickness of from 0.5 to 2 mm and a mass of less than 2 g, in particular less than 1 g.

A periodic shift of the two refractive elements relative to each other of approx. 50-100 Hz is possible without trouble.

In the case of the free-form elements (refractive element with free-form surface) moved laterally towards each other, the actuating elements for shifting the free-form elements can comprise for example piezo elements and a mechanical lever device for translating the vertical travel of the piezo elements. The elements can effect for example a resonant harmonic vibration. In this case, the periodic force of the actuator can serve merely to compensate for the attenuation losses, with the result that only very small forces are necessary, meaning that shocks can largely be prevented. The control of the Z-positions takes place in this case via the timing of the illumination pulse.

Alternatively, however, the elements can also be adjusted by the actuating elements to a quantity of discrete positions where in each case they are stationary for a short acquisition time interval T. As a result, even when continuous (unpulsed) illumination is used, motion blurring could be prevented, and any, e.g. equidistant, positions that correspond to equidistant Z-cross-sections in the object space can be set. However, this mode requires one acceleration and one deceleration per position, with the result that much greater forces must be at work, which can in turn bring about shocks at higher frequencies.

With the imaging system according to the invention, the optical component can be arranged in an area of the imaging lens system in which the ray beams coming from different field points largely overlap. In particular, the optical component can be positioned close to the aperture diaphragm of the imaging lens system or close to an image of the aperture diaphragm of the imaging lens system. This is advantageous in that the optical component then effects essentially only an alteration of the focal position.

Furthermore, the imaging lens system can have a collimated section in the beam path and the optical component can be arranged in the collimated section.

The imaging system furthermore preferably also has an illumination unit. In particular, the illumination unit can effect a pulsed illumination. Very short image acquisition times are possible through a pulsed illumination. In particular, it is not necessary to rely on mechanical diaphragms for an image acquisition sensor in order to realize short acquisition times. By means of the pulsed illumination, the acquisition time can be set substantially by the pulse duration.

Furthermore, the illumination unit can illuminate the object in different colours time-sequentially.

In particular, the time-sequential illumination by the illumination unit can be chosen such that, taking into account a longitudinal chromatic aberration of the imaging lens system and the precisely set refractive power of the optical component, the object can be recorded in the same depth with the different colours. The imaging lens system can thus be formed even without corrected longitudinal chromatic aberration, whereby for example it is possible to cut down on lenses. This reduces the costs for the imaging lens system and in addition also makes it even lighter.

By the same depth is meant here in particular a depth at which individual structures can still be identified in the pictures from the same depth, even if they are blurred. In particular the same depth is present when the distance is no greater than one Rayleigh unit (which corresponds to $\lambda/NA^2$).

Furthermore, the imaging system according to the invention can carry out two successive acquisitions, such that because of the different optical refractive power values of the optical component the two acquisitions lie within two Rayleigh units, in particular within one Rayleigh unit.

Furthermore, the imaging system can be formed e.g. as a microscope, telescope, binoculars, etc. Furthermore, the imaging system can be formed as a stereo imaging system (in particular a stereomicroscope).

For the case of the formation as a stereo imaging system, the optical component can preferably be arranged in the beam path common to both stereo channels.

The object is furthermore achieved by an imaging method in which an imaging lens system images an object into an image plane, wherein the imaging lens system contains an optical component for a higher depth of field, of which the refractive power is altered and the optical effect remains rotation-symmetrical.

Developments of the imaging method according to the invention are given in the dependent method claims.

In particular, the imaging method can be designed as a microscopy method and furthermore as a stereomicroscopy method.

It is understood that the features mentioned above and those yet to be explained below can be used, not only in the stated combinations, but also in other combinations or alone, without departing from the scope of the present invention.

The imaging system according to the invention can be developed in particular such that the imaging method according to the invention can be carried out (according to the described developments and also according to all described embodiments). In the same way, the imaging method according to the invention can be developed such that the imaging methods described in conjunction with the imaging system according to the invention (including its developments and the described embodiments) can be realized.

BRIEF DESCRIPTION OF THE DRAWINGS

The invention is explained in further detail below by way of example with reference to the attached drawings which also disclose features essential to the invention. There are shown in:

FIG. 7 a further embodiment of the imaging lens system for the case where the imaging system is formed as a stereomicroscope, wherein however the stereomicroscope has no switching element and the beam path through a first partial pupil is shown;

FIG. 8 a view according to FIG. 7, wherein the beam path through a second partial pupil is shown;

DETAILED DESCRIPTION

Figure 1:
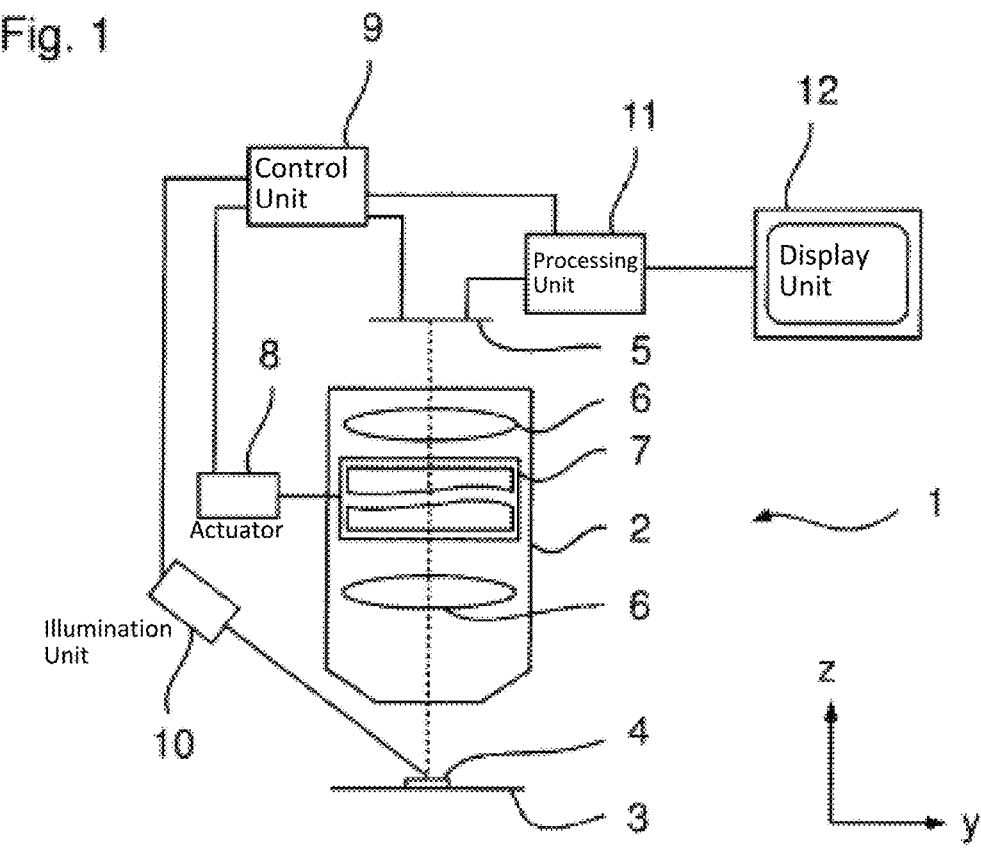
FIG. 1 a schematic view of an embodiment of the imaging system according to the invention.

In the embodiment shown in FIG. 1, the imaging system 1 according to the invention is formed as a microscope and has a schematically represented imaging lens system 2 with which an object 4 arranged on a specimen stage 3 of the microscope can be imaged into an image plane in which an image acquisition sensor 5 is positioned.

The imaging lens system 2 comprises an image lens system 6, represented schematically in FIG. 1 by two lenses, which effects the desired imaging, and an optical component 7, the refractive power of which is alterable while the optical effect of the optical component remains rotation-symmetrical.

Furthermore, the imaging system 1 comprises an actuator 8 for the optical component 7, a control unit 9, an illumination unit 10, an image processing unit 11 and a display unit 12.

As has already been described at the beginning, the depth of field in the object space is in principle coupled to the lateral resolution and tends to be too low for many fields of application.

In the at least approximately diffraction-limited case, the object-side lateral resolution (minimum resolvable structure width) is proportional to $\lambda/NA$ and the object-side longitudinal resolution (=depth of field) is proportional to $\lambda/NA^2$, wherein $\lambda$ is the wavelength of the light used and NA is the object-side numerical aperture of the imaging lens system 2. Thus the resolution of smaller structures requires an enlargement of the object-side NA, which then disadvantageously leads to a disproportionate decrease in the depth-of-field range in the object space (namely according to a quadratic law).

In order to now obtain a larger depth-of-field range in the object space, even with a high object-side numerical aperture (for resolving smaller structures), the optical component 7 is formed such that its refractive power can be varied, wherein pictures of the object 4 are taken for different refractive power values by means of the imaging lens system 2 and the image acquisition sensor 5. The variation in the refractive power of the optical component 7 now has the result that these pictures correspond to images from different z-planes of the object 4. In other words, a variation in the refractive power of the optical component 7 leads to a movement of the z-focal position during the image acquisition. The different pictures are delivered to the image processing unit 11. The image processing unit 11 evaluates all pictures in sections in respect of the existing sharpness of the picture and from them composes a complete image with a higher depth of field (compared with the depth of field of an individual picture). The complete image can then be represented by means of the display unit 12.

In order that sufficiently good pictures can be achieved, the optical component 7 is formed such that it always has approximately a rotation-symmetrical optical effect. An excellent imaging can thus be guaranteed, even if the refractive power is altered by means of the optical component 7.

The alteration of the refractive power of the optical component thus leads to an alteration of the focal length and back focal length of the imaging lens system, which leads to the desired movement of the z-focal position.

The optical component with variably adjustable refractive power here has two refractive elements 13, 14 (FIG. 2) which each comprise at least one free-form surface and can be shifted laterally relative to each other (here e.g. in y-direction and thus perpendicular to the optical axis). The optical component 7 can thus be formed e.g. as described in U.S. Pat. No. 3,305,294. It is shown there that by laterally shifting two elements which each have a flat surface and a free-form surface, wherein the free-form surface can be described by a Taylor polynomial in two variables, a rotation-symmetrical optical effect is achievable which can be used for providing a lens of variable refractive power.

In the embodiment described here, the two refractive elements 13 and 14 have a flat side 15, 17 each and a free-form surface 16, 18 each, which behave exactly mirror-symmetrical to each other in a zero position, with the result that the two elements 13 and 14 in the zero position form almost a coplanar plate. A pure defocusing effect can be brought about e.g. when the free-form surfaces can be described by the following third-order polynomial:

$$z(x, y) = k \cdot \left( x^2 \cdot y + \frac{y^3}{3} \right) \quad (1)$$

Here, it is assumed that the lateral shift of the elements 13, 14 takes place along the y-axis (if the shift is to take place along the x-axis, the roles of x and y in the above equation 1 are to be swapped accordingly). Furthermore, it is assumed that, to describe the polynomial, the simplified case with $k_2 = 0$ of the following formula (1') is used:

$$z(x, y) = k_1 \cdot \left(x^2 \cdot y + \frac{y^3}{3}\right) + k_2 \cdot y \qquad (1')$$

For ray beams incident parallel to the axis, the lateral shift of the two elements 13, 14 by a distance s thus brings about an alteration of the wavefront according to the following equation $$\Delta W(x, y) = k \cdot \left(2 \cdot s \cdot (x^2 + y^2) + 2 \cdot \frac{s^3}{3}\right), \qquad (2)$$

thus an alteration of the focal position plus a constant term (which is often also called a piston term). This piston term does not affect the imaging properties precisely when the optical component 7 is located in the infinite beam path. A positioning of the optical component 7 in an area of the imaging lens system with (at least approximately) collimated beam path is therefore preferred.

Figure 2:
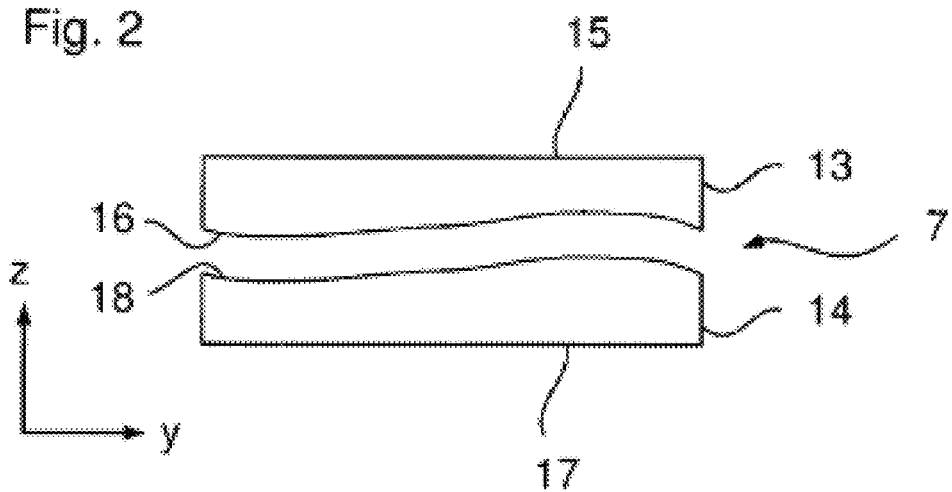
FIG. 2 an enlarged view of the optical component from FIG. 1.
Figure 3:
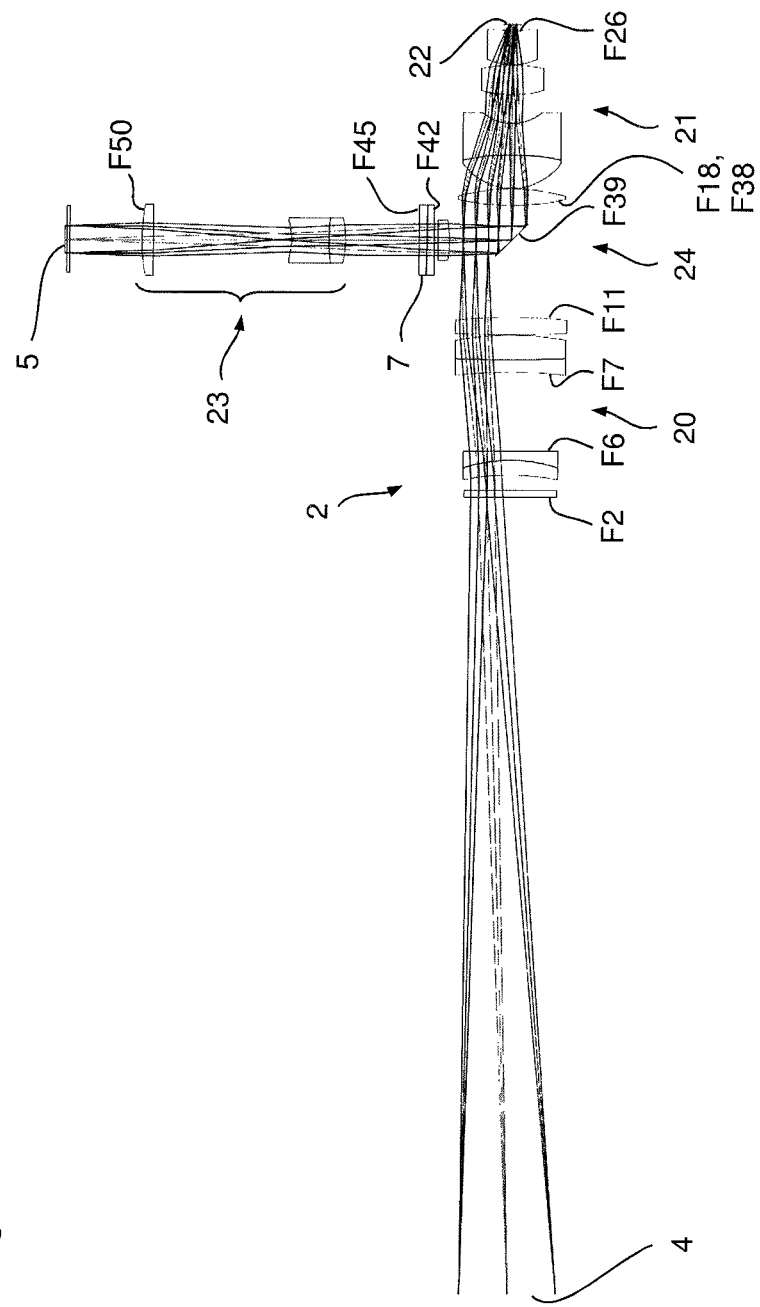
FIG. 3 a sectional view of the imaging lens system for the case where the imaging system according to the invention is formed as a stereomicroscope through one of the two stereo partial pupils, wherein the system is located in the position in which the optical component increases the focal plane distance by 10 mm.
Figure 4:
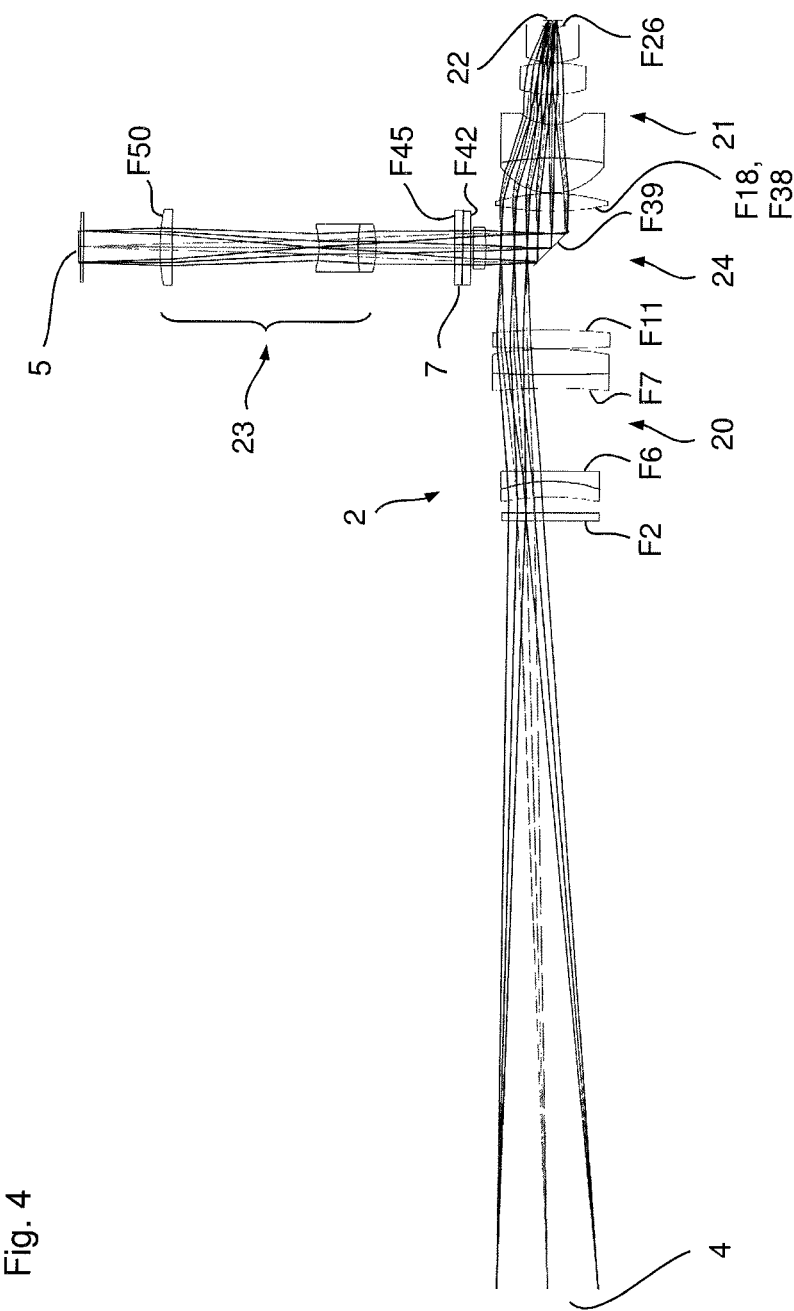
FIG. 4 a sectional view according to FIG. 3, wherein the optical component 7 reduces the focal plane distance by 10 mm.
Figure 5:
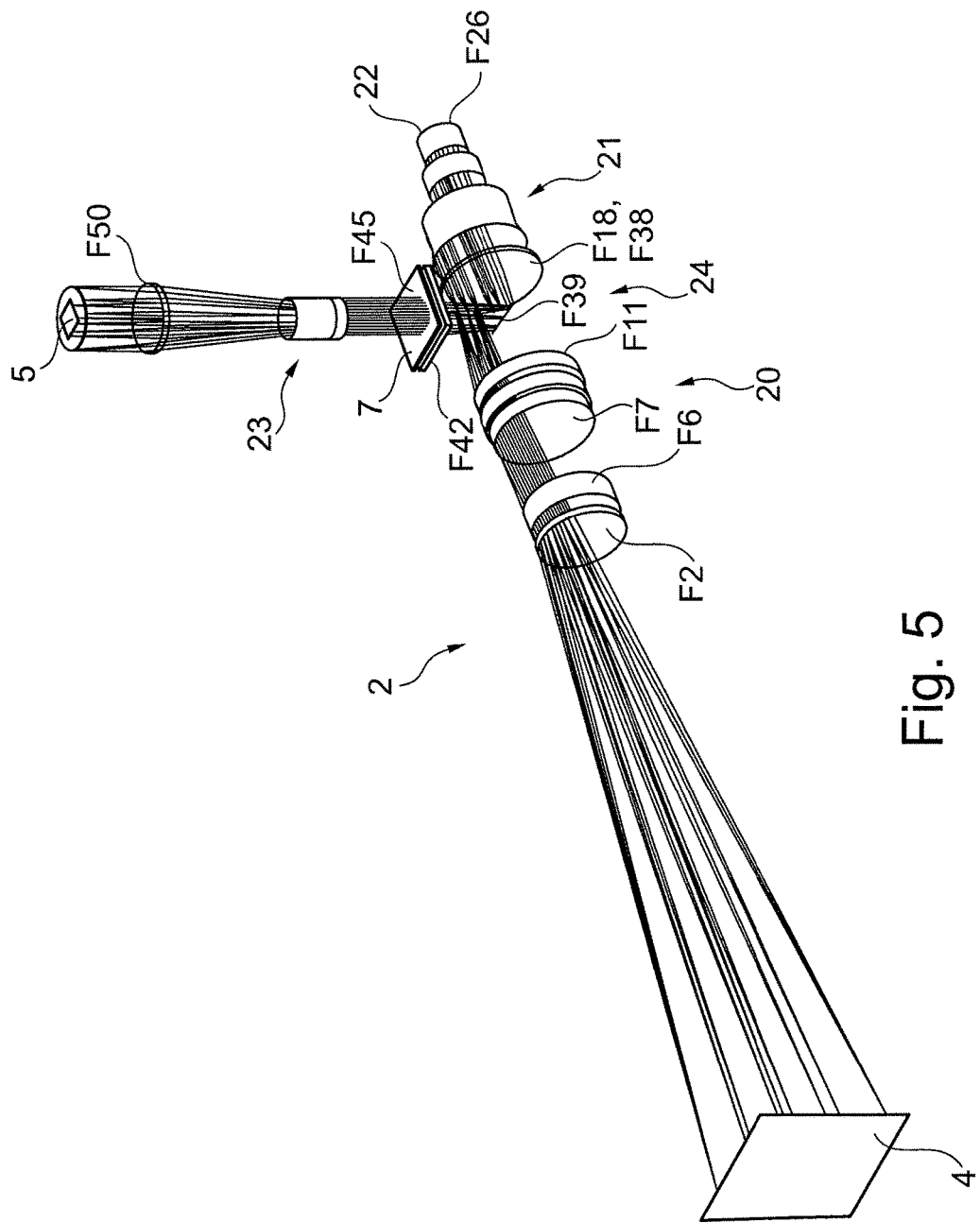
FIG. 5 a schematic spatial view of the whole imaging lens system as well as the focal plane and the acquisition sensor.
Figure 6:
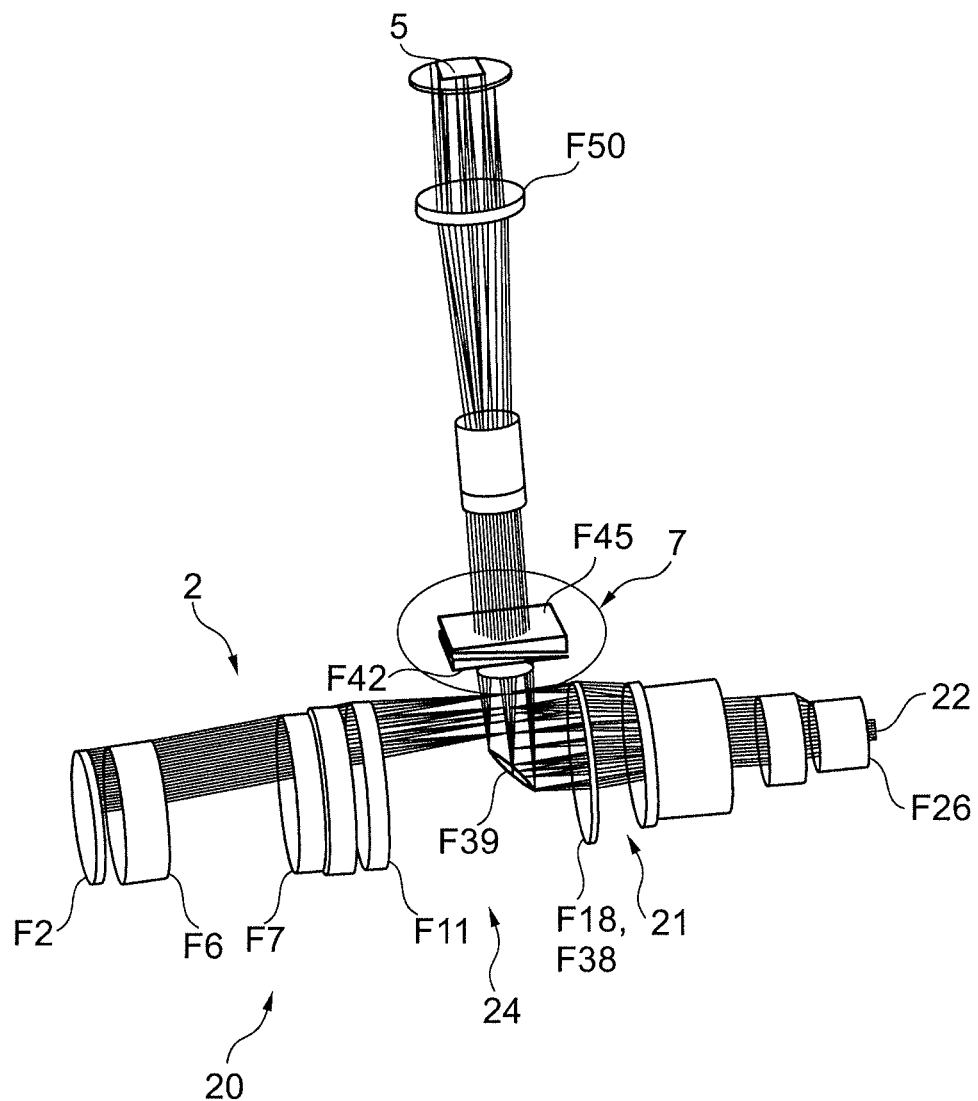
FIG. 6 an enlargement of a section from FIG. 5.

As can be seen in the schematically enlarged representation of FIG. 2, the two elements 13 and 14 movable relative to each other can be oriented such that their free-form surfaces 16, 18 face each other. In this case, it is particularly easy to carry out the adjustment of the zero position. For this, the distance between the two elements 13 and 14 must simply be reduced until the two elements 13, 14 touch. In this position, a centering then automatically takes place.

The distance between the two elements 13, 14 in axial direction can then be enlarged again precisely so far that the two elements 13, 14 do not quite touch during the lateral movement (in y-direction) during the functional operation.

However, it is also possible to orient the two elements 13, 14 such that their free-form surfaces 16, 18 face away from each other. In this way, the distance between the two elements 13, 14, which then face each other on the flat sides 15, 17, can be kept minimal. This has proved advantageous for the imaging quality in particular in the case of larger field and aperture angles on the transition surface between the two elements 13, 14.

It is furthermore possible for the free-form surfaces 16, 18 to additionally be able to have higher-order terms for influencing higher image errors. For example, a term of the form $$z(x, y) = k \cdot \left(y \cdot x^4 + \frac{2}{3} \cdot (x^2 \cdot y^3) + \frac{y^5}{3}\right) \qquad (3)$$

would predominantly influence the spherical aberration and could thus help to correct the spherical aberration that occurs, for example in the case of focusing into another specimen depth in an embedded object (e.g. in water or emulsion shells).

Furthermore, it is also possible for the flat sides 15, 17 of the two elements 13, 14 to be formed not exactly flat, but to also have an effective shape. For example, a symmetrical distribution of the surface profile for the free-form surface according to the above Formula 1 on the front and back of the element 13, 14 could have the effect that the profile depths on each of the surfaces remain very small, with the result that for example a photolithographic production of the elements 13, 14, in which typically only maximum profile depths in the range of from <10 to 30 μm are possible, is facilitated.

To prevent or reduce undesired reflexes or for easier producibility, a meniscus effect without refractive power can in addition also be superimposed, i.e. on the front and back of each element 13, 14 identical spherical curvatures of the surface are superimposed on the corresponding effective profile of the respective surface.

According to the invention, the optical component 7 with variable refractive power is preferably arranged at one point in the beam path of the imaging lens system 2 at which the ray beams coming from different field points of the object 4 largely overlap, such as for example close to an aperture diaphragm or the image of an aperture diaphragm, thus a system pupil. This has the effect that the variable refractive power effect in the first approximation produces a pure focusing and no field-dependent image errors. A preferred position of the optical component 7 fulfils the following condition $$\left|\frac{y_H}{y_R}\right| \le 0.5 \qquad (4)$$

and even more preferably the condition $$\left|\frac{y_H}{y_R}\right| \le 0.2 \qquad (5)$$

Here, $y_H$ is the incident height of a main beam (thus a beam through the centre of the aperture diaphragm) of a field point at a maximum radial distance from the optical axis of the imaging lens system 2 and $y_R$ is the incident height of a marginal beam coming from an object point on the optical axis (thus a beam through the edge of the aperture diaphragm). It is particularly advantageous if this condition (according to one of the two indicated inequalities 4, 5) is realized at the same time as the already named condition of the preferred positioning in the collimated beam path, i.e. when the optical component 7 is positioned close to a system pupil of the imaging lens system 2 and at the same time in the collimated beam path. This is the case in the embodiments yet to be described below in connection with FIGS. 3 to 10.

If the imaging system 1 is formed as a stereo imaging system (for example a stereomicroscope), the optical component 7 with variable refractive power can preferably lie in the area of a common main objective lens, thus the subsystem of the imaging lens system which precedes the system diaphragms defining the partial bundles and is passed through by all partial bundles together. In this case, the stereoscopic viewing angle (thus the angle between the main beams of a viewed object point) changes as a function of the respective z-position of this object point according to the same principle as in the case of direct visual observation of an object with corresponding subsequent accommodation of the eyes. This succeeds in keeping two specific depth information stimuli of the natural vision process consistent with each other, namely accommodation and divergence stimuli.

This is also advantageous in particular if the stereoscopic imaging system 1 is formed such that a direct visual observation is also possible. However, this is advantageous even in the case of a digital image acquisition (for example by two cameras or also time-sequentially by means of a single camera) followed by representation of the stereoscopic images on a suitable display means, such as e.g. an autostereoscopic display.

The stereoscopic images can then be interpreted more easily in the observer's visual cortex and the observer does not experience any premature fatigue.

Naturally, it is possible for this positioning named as preferable to be present in the area of the common main objective lens at the same time as the advantageous positioning in the collimated beam path and/or close to a system pupil according to the above inequalities.

The image acquisition sensor can be e.g. a CCD or a CMOS sensor. If necessary, a colour filter mask, such as e.g. a Bayer mask, can be arranged upstream of this sensor. Naturally, it is also possible to provide several sensors for different colour channels, with the result that the individual colour channels can be recorded at the same time. Furthermore, another special intermediate or adapter lens system can be provided in front of the image acquisition sensor 6.

The object 4 is exposed to the (for example multi-coloured) light of the illumination unit 10, wherein the illumination unit 10 is preferably formed as a pulsed light source (such as e.g. a semiconductor light source). It is thereby possible to provide the quantity of light desired for producing low-noise images (lumen*second) per pixel within a very small time window of e.g. less than one millisecond. The shorter the acquisition period is, the lower the motion blurring, or the more precisely a picture represents in each case a particular z-position within the object volume if the optical component 7 continuously alters its refractive power, which is preferred.

In the imaging system 1 according to the invention, a real-time image can be represented on the display unit 12, thus an image with a sufficient frame rate such that for an observer movements seem to flow naturally and the image does not flicker. For this, a frame frequency of more than 50 Hz and preferably more than 75 Hz is desired. In the following, the frame rate of the display unit 12 is denoted by $F_A$ and the corresponding period by $T_A$.

In order that, within a display frame or display of a frame, image information from several different z-planes is available, the image acquisition sensor 5 functions with an n-times higher image acquisition frame rate, which is denoted by $F_K$ in the following. The associated period is denoted by $T_K$. By a precise synchronization of $F_K$ to a half-integral or integral multiple of the adjustment frequency of the optical component 7 it can be achieved that the image acquisition sensor 5 in each case provides partial images from exactly the same z-planes, which the image unit 11 evaluates to produce the complete image with higher depth of field.

In the case of a half-integral multiple of the adjustment frequency of the optical component 7 with variable refractive power, it is possible for the image acquisition sensor 5 to record, on the forward and return path of the adjustment of the refractive power of the optical component 7, in each case all partial z-images required for a complete display image, roughly analogously to the interlaced scanning or interlacing method from television technology. The advantage is that as a result a sufficient number of intermediate positions in z-direction can nevertheless be recorded with a limited frame rate of the image acquisition sensor 5.

The setting is preferably chosen such that two successive pictures are spaced apart from each other in z-direction by no more than one Rayleigh length ($=\lambda/NA^2$). It is thus ensured that the same sections of the object 4 in the two pictures, even if they are represented a little blurred, can still be identified as such by the image processing unit 11.

It is also possible for the time window of the integration times of the image acquisition sensor to be arranged not equidistant on the time axis. Thus it is advantageous e.g. if the lateral shift of the two elements 13 and 14 of the optical component 7 represents a continuous movement and (approximately), as far as possible, even a harmonic vibration. In this way, the acceleration and deceleration forces that occur on the elements 13 and 14 themselves and on the mechanical components absorbing the forces (such as e.g. the actuator 8) are minimized, with the result that undesired degradations of the image quality as a result of surface distortions or unintended positional deviations are minimized.

In the case of a harmonic vibration, the lateral elongation of the elements 13 and 14 and the time are linked by a cosine law. The functional dependency of the z-position of the focus on the lateral elongation of the elements 13 and 14 generally depends on the precise shape of the free-form surfaces 16, 18. In the simplest (and indeed also the most frequent) case, there is a lateral relationship here.

To ensure an equidistant recorded image sequence of the object in the depth (and thus in z-direction), the starting times for the image acquisition time window of the image acquisition sensor 5 or for the illumination pulses of the illumination unit 10 are defined inversely to the z-elongation of the focal plane as a function of the time, thus in the case of harmonic z-scan movement according to an arc cosine function. The pictures recorded in the various z-positions (because of the varying refractive power of the optical component 7) by means of the image acquisition sensor 5 are transmitted to the image processing unit 11 and then combined in each case to form a complete image with a high depth of field (its depth of field is greater than the depth of field of an individual picture) which represents a partial mage (frame) on the display unit 12.

The image processing algorithm to be applied for this can be divided e.g. into two processing steps:

In a first step, a quantification of the local image sharpness or the local image contrast takes place in each individual picture, also called partial z-images below. Corresponding base algorithms are known from the state of the art, for example from the field of autofocus devices.

Thus it is possible to use e.g. the effect that in a sharply defined image section of a partial z-image the Fourier transform of the autocorrelation contains much higher spatial frequency components than in a defocused image section.

Such an algorithm can be implemented as software and/or hardware.

A second step consists of selecting the most sharply defined image section in each case from all n partial z-images for each local image section for the desired complete image and combining them into a complete image. This step can also be implemented as software and/or hardware.

In addition, if desired and/or necessary, a so-called registration step can also be carried out in which e.g. an adaptation of the image scales, the translation and/or the rotation of the partial z-images is carried out.

Such a step can be necessary for example in order to compensate again for the alteration of the image scale dependent on the focal position of the element with variable refractive power and thus on the Z-position of the partial image in the object space. The partial Z-images are scaled to the same scale before the processing to form a complete image with a high depth of field.

For the pulsed illumination of the object 4 by means of the illumination unit 10, the latter can have e.g. several semiconductor light sources of different wavelength ranges (for example separate LEDs with the colours red, green and blue). The time-sequential illumination with the different colours is carried out in particular for a direct perception so quickly that from an observer's point of view the colour components mix to form an almost white illumination because of the inertia of the eye. An advantage of the use of known colour channels is e.g. that the colour temperature can be precisely adapted.

If the wavelength bands for the individual coloured light sources (coloured LED or coloured lasers) are not intrinsically too broad spectrally, the focal deviation of the respective colour partial images (caused by the longitudinal chromatic aberration of the imaging lens system 2) can be compensated for by recording the colour partial images staggered in time relative to each other.

A corresponding shift of the focal position corresponding to the scan movement of the optical component 7 corresponds to a temporal shift between the acquisition time points of the various coloured partial images. It is therefore possible to adjust the temporal shift between the illumination time points of the various coloured light sources such that they produce in each case a sharply defined colour partial image of one and the same object structure (seen in z-direction) on the image acquisition sensor 5. By one and the same object structure seen in z-direction is meant in particular an object structure which lies within one Rayleigh unit.

It is thereby possible to reduce or compensate for longitudinal chromatic aberrations of the imaging lens systems 2. In particular, a chromatically uncorrected imaging lens system 2 can be provided the production outlay for which is greatly simplified and which can nevertheless be used for polychromatic imaging purposes.

A further advantage of the described partially sequential illumination with different colours is that, if only one image acquisition sensor 5 is provided, a colour mask is no longer necessary and a better spatial resolution can thereby be achieved with the image acquisition sensor 5. The total pixel number for the image acquisition can then namely be used for each colour partial image.

As already mentioned, an improved depth of field can be offered to the user with the imaging system according to the invention, which is advantageous in the case of stereoscopic images and/or when a stereoscopic observation is possible.

FIGS. 3 to 6 show the optical structure of the imaging lens system 2 for the case where the imaging system 1 according to the invention is formed as a stereomicroscope. The optical component 7 is part of an optical basic arrangement of the imaging lens system 2, which has a main objective lens 20 (fixed focal length or varioscope), an intermediate imaging lens system 21, a switching element 22 (e.g. DMD) and a camera adapter lens system 23. The main objective lens 20 images an object plane 4 in the object-side focal plane of the main objective lens 20 to infinity.

In the area 24 behind the main objective lens 20, in the collimated beam path ("diaphragm plane"), there is a dividing device (not shown) for defining the partial pupils, thus the two or more than two partial pupils, from which the suitable stereobase is derived for a main observer and optionally one or more co-observers. This dividing device comprises, quite generally speaking, any element influencing light transmission which cuts the two or more partial pupils out of the overall pupil of the main objective lens 20. In the simplest case, the dividing device comprises one or more pairs of pinhole diaphragms at a respectively fixed distance from the axis of the main objective lens 20. The dividing device can then be formed rotatable about the objective lens axis in order to be able to rotate the stereobase accordingly. However, it is also possible for the dividing device to comprise several diaphragm elements, for example two diaphragm holders rotatable in opposite directions, with the result that two stereo perspectives rotatable in opposite directions can be produced.

As an alternative to the pinhole diaphragms, the dividing device for forming the partial pupils can also comprise any elements, such as e.g. LC shutters, which switch the light transmission depending on position.

Behind the diaphragm plane there is the relay lens system 21 which is passed through twice by the light bundles used for the imaging: In the first pass, the light bundles formed in the diaphragm plane are imaged onto the switching element 22 (in the specific case a tilting mirror matrix or DMD).

The light reflected at the switching element 22 then passes through the relay lens system 21 on another path (preferably: a light path running symmetrically to the axis of the main objective lens 20) back into the diaphragm plane and is there deflected by a stationary deflecting element 25 (here: a flat mirror) by a fixed angle (here: 90°).

Behind the stationary deflecting element 25, but still close to same, there is the optical component 7 with variable refractive power.

The camera adapter lens system 23 then images the ray beams onto the image acquisition sensor 5. In the example described here, this is a sensor with a Bayer mask for colour selection. Of course, it could however equally well be a camera with three image sensors and colour splitter prisms or the like.

The imaging lens system 2 here has the following specification data:

| | |
|---|---|
| Object field size = | 27 mm × 48 mm |
| Diameter of the partial pupils | 7 mm |
| Distance between the partial pupil centres = | 20 mm |
| Surface area on the tilting mirror matrix 26 = | 1.76 mm × 1.00 mm |
| Dimensions of camera-sensor 5 = | 14.4 mm × 8.1 mm (⅔"-sensor) |
| Angle of incidence of the main beams = tilt angle of the micromirrors of the tilting mirror matrix = | 12° |
| Wavelength range = | 400-700 nm (visible spectral range) |
| Focal length of main objective lens 20 = | 336.88 mm |
| Focal length of intermediate imaging lens system 24 = | 24.569 mm |
| Focal length of camera adapter lens system 23 = | 100.03 mm |

The design data for the three optical partial systems 20, 21 and 23 of the imaging lens system 2 according to the invention are given below (all details in millimeters). For reasons of clarity the surfaces passed through twice are also listed twice, wherein to simplify the representation in FIGS. 3-6 the corresponding reference numbers are not given for all surfaces and diaphragms are not drawn in.

The representation follows the conventions, in particular the sign conventions, of the optical design program CodeV which is sold by Optical Research Associates, Pasadena, Calif., USA. This means in particular:

A positive/negative radius signifies that the centre of curvature lies to the right/left of the surface apex.

Surface decentrations are given by the three shifts XDE, YDE and ZDE in the three directions x, y and z relative to the apex coordinate system of the centred surface.

Surface tilts are given by three angles of rotation ADE, BDE and CDE about the local x-, y- and z-axes in the apex coordinate system, wherein the rotations are generally to be carried out in the indicated sequence.

Aspherical surfaces are described by the development coefficients A, B, C and D, as well as the conic section constant k according to the following surface equation:

$$z = \frac{(x^2+y^2)/R}{1+\sqrt{1-(1+k)\cdot\frac{(x^2+y^2)}{R^2}}} + A\cdot(x^2+y^2)^2 + B\cdot(x^2+y^2)^3 + C\cdot(x^2+y^2)^4 + D\cdot(x^2+y^2)^5$$

Free-form surfaces are defined by the following surface equation $$z = \frac{(x^2+y^2)/R}{1+\sqrt{1-(1+k)\cdot\frac{(x^2+y^2)}{R^2}}} + \sum_{i,j} C_{ij}\cdot x^i y^j$$

The optical data are given rounded to 3 (thicknesses, Abbe numbers), 5 (radii) or 6 (refractive indices, aspherical constants) decimal places. Allowance is thereby to be made for the fact that for example further decimal places for the thickness could be seen as random and not essential, while e.g. the aspherical coefficients must be given more precisely, in order that the example can be reproduced in an optics program.

The types of glass indicated in the example are in each case to be seen as representatives for a broad equivalence range of types of glass coming into consideration.

The coefficients of the free-form elements 13, 14 only comprise the lowest orders that are needed to produce a refocusing. This prevents the optical component 7 with variable refractive power used from compensating for specific individual imaging errors of the main objective lens 20 (used here only by way of example) and thus from being tied to the use with this particular main objective lens 20. However, the values for the coefficients themselves have been determined from an optimization calculation and therefore deviate minimally from the relationship to be expected according to the teaching of U.S. Pat. No. 3,305,294 (e.g. the coefficient of C(2.1) is approximately, but not quite exactly, three times as large as C(0.3)).

| Surface no. | Radius | Thickness | Type of glass |
|---|---|---|---|
| Object plane | ∞ | variable | |
| F2 | ∞ | 2.000 | NBK7 |
| F3 | ∞ | 4.400 | |
| F4 | – | 4.200 | NSF6 |
| F5 | −40.098000 | 2.600 | NSSK8 |
| F6 | ∞ | 22.500 | |
| F7 | −158.49000 | 3.600 | NSF6 |
| F8 | 370.47000 | 7.000 | NSK2_SCHOTT |
| F9 | 82.93700 | 0.100 | |
| F10 | 258.52000 | 5.000 | NSK5_SCHOTT |
| F11 | −145.38000 | 3.000 | |

-continued

| | | | |
|---|---|---|---|
| F12 | | 19.000 | |
| F13 | ∞ | 0.000 | |
| XDE: 0.000 YDE: 10.000 ZDE: 0.000 | | | |
| Diaphragm | ∞ | 0.000 | |
| F15 | ∞ | 0.000 | |
| XDE: 0.000 YDE: −10.000 ZDE: 0.000 | | | |
| F16 | ∞ | 0.000 | |
| F17 | ∞ | 10.000 | |
| F18 | 69.32807 | 4.800 | SFPL53 |
| F19 | −45.75941 | 0.100 | |
| Asphere: K: 0.00000 A: 0.728465E−05 B: −.732705E−08 | | | |
| C: 0.274418E−10 D: −.624797E−13 | | | |
| F20 | 16.81987 | 9.500 | SFPL53 |
| F21 | −71.15723 | 9.000 | SF1 |
| F22 | 12.89428 | 8.160 | |
| F23 | 29.22417 | 8.500 | SNPH2 |
| F24 | −40.84553 | 0.100 | |
| F25 | 17.81600 | 9.500 | SNPH2 |
| F26 | 11.36370 | 2.000 | |
| F27 | ∞ | 0.000 | |
| Tilting mirror 22 | ∞ | | |
| F29 | ∞ | −2.000 | |
| F30 | 11.36370 | −9.500 | SNPH2 |
| F31 | 17.81600 | −0.100 | |
| F32 | −40.84553 | −8.500 | SNPH2 |
| F33 | 29.22417 | −8.160 | |
| F34 | 12.89428 | −9.000 | SF1 |
| F35 | −71.15723 | −9.500 | SFPL53 |
| F36 | 16.81987 | −0.100 | |
| F37 | −45.75941 | −4.800 | SFPL53 |
| Asphere: K: 0.00000 A: 0.728465E−05 B: −.732705E−08 | | | |
| C: 0.274418E−10 D: −.624797E−13 | | | |
| F38 | 69.32807 | −10.000 | |
| F39 | ∞ | 17.533614 | REFL (deflecting element 25) |
| ADE: 45.000 BDE: 0.000 CDE: 0.000 | | | |
| F40 | 47.93658 | 3.2000 | NFK5 |
| F41 | −1129.18109 | 1.0000 | |
| F42 | ∞ | 2.000 | NFK5 |
| F43 | ∞ | 0.140 | |
| Free-form surface 18: C(2.1) = 0.0009804 C(0.3) = 0.0003041 | | | |
| F44 | ∞ | 2.000 | NFK5 |
| Free-form surface 16: C(2.1) = 0.0009804 C(0.3) = 0.0003041 | | | |
| F45 | ∞ | 21.000 | |
| F46 | 27.46389 | 4.800 | SFPL51 |
| F47 | −42.51268 | 10.500 | NKZFS4 |
| F48 | 20.49002 | 39.000 | |
| F49 | ∞ | 3.2000 | NLASF43 |
| F50 | −56.20738 | 20.300 | |
| F51 | ∞ | 1.0000 | NBK7 |
| F52 | ∞ | 0.5000 | |
| Image plane | ∞ | 0.000 | |

Refractive indices of the types of glass used

| | | Refractive index at wavelength (nm): | | |
|---|---|---|---|---|
| Type of glass | Manufacturer | 656.00 | 546.00 | 486.00 |
| NBK7 | SCHOTT | 1.514331 | 1.518726 | 1.522386 |
| NSF6 | SCHOTT | 1.796109 | 1.812674 | 1.827871 |
| NSSK8 | SCHOTT | 1.614023 | 1.620682 | 1.626423 |
| NSK2 | SCHOTT | 1.604146 | 1.609942 | 1.614870 |
| NSK5 | SCHOTT | 1.586203 | 1.591429 | 1.595820 |
| SNPH2 | OHARA | 1.909203 | 1.934313 | 1.958060 |
| SEPL53 | OHARA | 1.437338 | 1.439856 | 1.441960 |
| SF1 | SCHOTT | 1.710337 | 1.723116 | 1.734651 |
| SFPL51 | OHARA | 1.495143 | 1.498457 | 1.501238 |
| NKZFS4 | SCHOTT | 1.609231 | 1.616645 | 1.623019 |
| NLASF43 | SCHOTT | 1.800221 | 1.810822 | 1.820076 |
| NFK5 | SCHOTT | 1.485353 | 1.489147 | 1.492278 |

The path traveled by the refractive elements 13 and 14 here is ±50 μm at a frequency of approx. 60 Hz. The area used for the imaging has a diameter of approx. 10 mm.

In a further embodiment according to FIGS. 7 to 10, no switching element (e.g. DMD) according to the embodiment of FIGS. 3 to 6 is needed. Instead, either a beam splitter or two cameras are required for the stereoscopic image acquisition.

The structure of the imaging lens system 2 again comprises a common main objective lens 20 (with fixed focal length or as a varioscope), which images the application plane 4 lying in the front focal plane of the main objective lens 20 and thus the object 4 essentially to infinity, a diaphragm plane located behind this, as well as lens systems arranged behind this which image the light bundles of each partial pupil onto one camera sensor each.

Unlike in the embodiment according to FIGS. 3 to 6, the beam path here thus branches behind the diaphragm plane into one distinct imaging path each per partial pupil.

The camera adapter lens system 23 shown here to the left of the main objective lens 20 and the camera or the image acquisition sensor 5 itself thus have to be present twice, one for each partial pupil. As a result, no switching element is needed and the light-conductance value of the arrangement can be correspondingly higher. On the other hand, the outlay is increased by the need for two cameras and the possibility of adaptations to the stereobase is limited.

For illustration, FIG. 7 shows the structure with the beam path through a first partial pupil and FIG. 8 shows the beam path through a second partial pupil.

Figure 9:
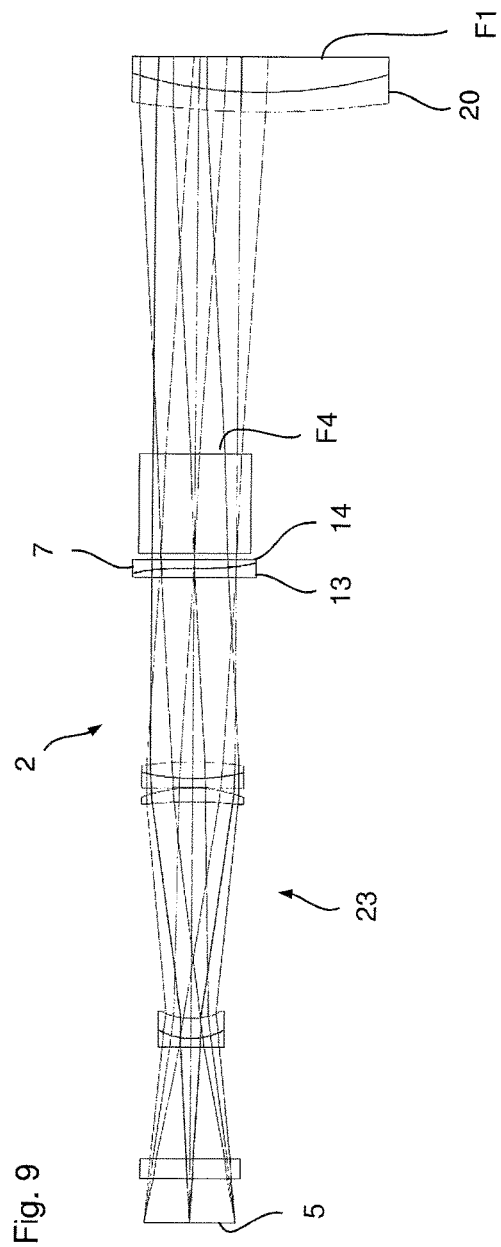
FIG. 9 an enlarged representation of a section from FIG. 7.

The optical component 7 with variable refractive power, which can also be called refocusing element, is here also located close to the diaphragm plane, as can be seen in FIG. 9 which shows an enlarged section from FIG. 7.

Figure 10:
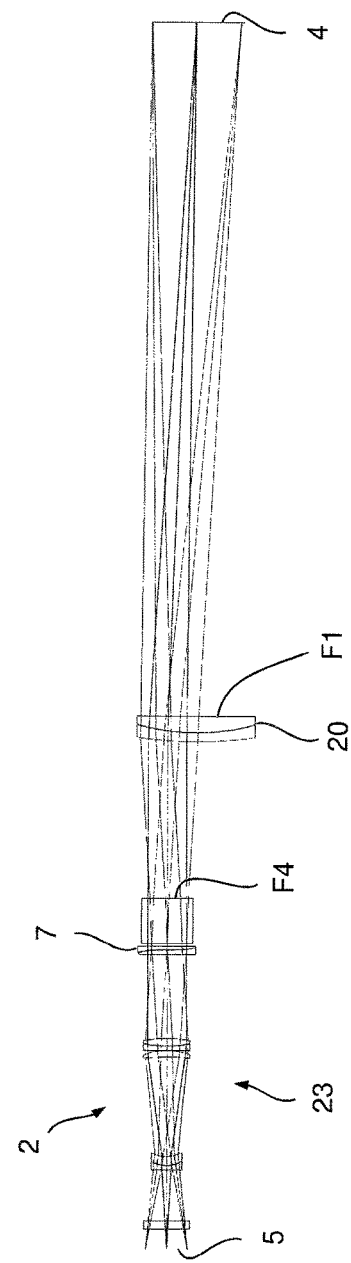
FIG. 10 a representation according to FIG. 7, wherein the focal plane in air has been moved by 20 mm in the direction of the main objective lens 20 by means of the optical component 7.

FIG. 10 shows the same section as FIG. 7 in a setting in which the focal plane in air has been moved by 20 mm in the direction of the main objective lens 20. The two free-form elements 13, 14 are shifted laterally towards each other by 0.05 mm. Accordingly, there is, in mirror image, a position (not shown) in which the focal plane is moved away from the main objective lens by the same amount, as well as corresponding intermediate positions.

The optical data of the embodiment according to FIGS. 7 to 10 are given below, wherein the same definitions and conventions as above are followed. Again, not all surfaces are provided with the corresponding reference numbers in FIGS. 7 to 10 and diaphragms are not drawn in.

The optical data are given rounded to 3 (thicknesses, Abbe numbers), 5 (radii) or 6 (refractive indices, aspherical constants) decimal places.

| Surface no. | Radius | Thickness | Type of glass |
|---|---|---|---|
| Object plane | ∞ | variable | |
| F1 | ∞ | 6.500 | NSSK8 |
| F2 | −79.945 | 3.500 | NSF10 |
| F3 | −154.877 | 10.000 | |
| F4 | ∞ | 48.500 | |
| XDE: 0.000 YDE: 11.000 ZDE: 0.000 | | | |
| F5 | ∞ | 3.000 | |
| F6 | ∞ | 18.000 | NBK7 |
| F7 | ∞ | 1.000 | |
| Diaphragm | ∞ | 0.000 | |
| F9 | ∞ | 0.000 | |
| XDE: 0.000 YDE: 0.050 ZDE: 0.000 | | | |
| F10 | ∞ | 1.500 | NLASF44 |
| F11 | ∞ | 0.000 | |
| Free-form surface 18: C(2.1) = 1.3425E−03 C(1.3) = 4.5295E−04 | | | |
| F12 | ∞ | 0.000 | |
| XDE: 0.000 YDE: −0.050 ZDE: 0.000 | | | |
| F13 | ∞ | 0.1400 | |
| F14 | ∞ | 0.000000 | |
| XDE: 0.000 YDE: −0.050 ZDE: 0.000 | | | |
| F15 | ∞ | 1.500 | NLASF44 |
| Free-form surface 16: C(2.1) = 1.3425E−03 C(1.3) = 4.5295E−04 | | | |
| F16 | ∞ | 0.000 | |
| F17 | ∞ | 0.000 | |
| XDE: 0.000 YDE: 0.050 ZDE: 0.000 | | | |
| F18 | ∞ | 30.000 | |
| F19 | 52.330 | 3.0000 | SFPL51 |
| F20 | −39.811 | 1.6000 | NKZFS4 |
| F21 | 260.390 | 0.100 | |
| F22 | 25.483 | 2.500 | SFPL51 |
| F23 | 84.140 | 39.097 | |
| F24 | −11.631 | 3.600 | NSF6 |
| F25 | −11.631 | 1.600 | SFPL51 |
| F26 | ∞ | 20.000 | |
| F27 | ∞ | 3.5000 | NBK7 |
| F28 | ∞ | 8.000 | |
| F29 | ∞ | 0.000 | |
| Image plane | ∞ | 0.000 | |

Refractive indices of the types of glass used:

| Type of glass | Manufacturer | Refractive index at wavelength (nm) | | |
|---|---|---|---|---|
| | | 656.00 | 546.00 | 486.00 |
| NBK7 | SCHOTT | 1.514331 | 1.518726 | 1.522386 |
| NSSK8 | SCHOTT | 1.614023 | 1.620682 | 1.626423 |
| NSF10 | SCHOTT | 1.720931 | 1.734311 | 1.746464 |
| NLASF44 | SCHOTT | 1.799026 | 1.808324 | 1.816324 |
| SFPL51 | OHARA | 1.495143 | 1.498457 | 1.501238 |
| NKZFS4 | SCHOTT | 1.609231 | 1.616645 | 1.623019 |
| NSF6 | SCHOTT | 1.796109 | 1.812674 | 1.827871 |

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. An imaging system, comprising:
   an imaging lens system for generating an image of an object in an image plane, including
      an optical component having an alterable refractive power and a rotation-symmetrical optical effect; and
      an illumination unit which illuminates the object with a pulsed illumination effect,
   wherein the optical component comprises two refractive elements, each having at least one free-form surface, and
   wherein the two refractive elements are displaceable relative to each other such that an entirety of the first of the two refractive elements is shifted with respect to the second of the two refractive elements, the displacement being in a direction transverse to an optical axis of the imaging lens system to alter the refractive power.

2. The imaging system according to claim 1, further comprising an image acquisition unit which records a plurality of images of the object each with a different refractive power value of the optical component in the image plane and conveys the plurality of images to an image processing unit which, using the plurality of the images, produces a complete image of the object with higher depth of field compared with one of the plurality of images.

3. The imaging system according to claim 1, wherein which the refractive power of the optical component is continuously alterable.

4. The imaging system according to claim 1, wherein the optical component is arranged in an area of the imaging lens system in which the ray beams coming from a plurality of different field points largely overlap.

5. The imaging system according to claim 1, wherein the optical component is positioned adjacent to either an aperture diaphragm of the imaging lens system or an image of the aperture diaphragm of the imaging lens system.

6. The imaging system according to claim 1, wherein the imaging lens system includes a collimated section in the beam path and the optical component is disposed in the collimated section.

7. The imaging system according to claim 1, wherein the illumination unit time-sequentially illuminates the object in each of a plurality of different colours.

8. The imaging system according to claim 7, wherein the time-sequential illumination by the illumination unit is chosen such that, taking into account a longitudinal chromatic aberration of the imaging lens system and the set refractive power of the optical component, the object is recorded in the same depth with each of the plurality of different colours.

9. The imaging system according to claim 1, wherein the optical component comprises a plurality of different optical refractive power values selected such that two successive image acquisitions lie within two Rayleigh units.

10. The imaging system according to claim 1, wherein the imaging system is configured as a stereo imaging system having two stereo channels.

11. The imaging system according to claim 10, wherein the optical component is disposed in a beam path common to both stereo channels.

12. The imaging system according to claim 1, wherein no further optical elements are arranged between the two refractive elements.

13. An imaging method for generating an image of an object in an image plane with an imaging lens system, the imaging lens system including an optical component, the optical component comprising two refractive elements which each have at least one free-form surface, the method comprising:
 altering the refractive power of the imaging lens system;
 maintaining rotation-symmetrical of the optical effect;
 pulsing illumination of the object; and
 shifting an entirety of a first of the two refractive elements relative to a second of the two refractive elements transverse to an optical axis of the imaging lens system to alter the refractive power.

14. The method according to claim 13, further comprising recording a plurality of images of the object with different refractive power values of the optical component; and using the plurality of images to generate a complete image of the object having a higher depth of field compared with one of the plurality of images.

15. The method according to claim 13, further comprising continuously altering the refractive power of the optical component.

16. The method according to claim 13, further comprising disposing the optical component in an area of the imaging lens system in which the ray beams coming from different field points largely overlap.

17. The method according to claim 13, further comprising positioning the optical component adjacent to either the aperture diaphragm of the imaging lens system or an image of the aperture diaphragm of the imaging lens system.

18. The method according to claim 13, further comprising disposing the optical component in a collimated section of a beam path of the imaging lens system.

19. The method according to claim 13, further comprising time-sequentially illuminating the object in each of a plurality of different colours.

20. The method according to claim 19, selecting the time-sequential illumination such that, taking into account a longitudinal chromatic aberration of the imaging lens system and a set refraction power of the optical component, the object is recorded in the same depth with each of the plurality of different colours.

21. The method according to claim 13, further comprising performing two successive image acquisitions such that, because of the different optical refractive power values of the optical component, the two image acquisitions lie within two Rayleigh units.

22. The method according to claim 13, wherein the imaging method comprises a stereo imaging method using two stereo channels.

23. The method according to claim 22, further comprising disposing the optical component in a beam path common to both stereo channels.

24. An imaging system, comprising:
 an imaging lens system for generating an image of an object in an image plane, including an optical component having an alterable refractive power and a rotation-symmetrical optical effect; and
 an illumination unit which illuminates the object with a pulsed illumination effect,
 wherein the optical component comprises two refractive elements, each having at least one free-form surface, wherein the at least one free form surface of one of the two refractive elements has a different shape than the at least one free form surface of the second of the two refractive elements, and
 wherein the two refractive elements are displaceable relative to each other in a direction transverse to an optical axis of the imaging lens system to alter the refractive power.

25. An imaging method for generating an image of an object in an image plane with an imaging lens system, the imaging lens system including an optical component, the optical component comprising two refractive elements which each have at least one free-form surface, the method comprising:
 altering the refractive power of the imaging lens system;
 maintaining rotation-symmetrical of the optical effect;
 pulsing illumination of the object; and
 shifting the two refractive elements relative to each other transverse to an optical axis of the imaging lens system to alter the refractive power, wherein the at least one free form surface of one of the two refractive elements has a different shape than the at least one free form surface of the second of the two refractive elements.

\* \* \* \* \*

UNITED STATES PATENT AND TRADEMARK OFFICE
CERTIFICATE OF CORRECTION

PATENT NO. : 10,048,484 B2  
APPLICATION NO. : 13/977683  
DATED : August 14, 2018  
INVENTOR(S) : Marco Pretorius et al.

Page 1 of 1

It is certified that error appears in the above-identified patent and that said Letters Patent is hereby corrected as shown below:

In the Specification

Column 9, Line 30: Delete "centering" and replace with --centring--.

Column 11, Line 20: Delete "6" and replace with --5--.

Column 12, Line 37: Delete "mage" and replace with --image--.

Column 14, Line 40: Delete "Diameter of the partial pupils       7 mm" and replace with --Diameter of the partial pupils       = 7 mm--.

Column 14, Line 59: Delete "millimeters" and replace with --millimetres--.

Column 15, Line 60: Delete "F4       ----     4.200    NSF6" and replace with --F4     -61.748       4.200    NSF6--.

Column 16, Line 58: Delete "SEPL53" and replace with --SFPL53--.

Column 16, Line 65: Delete "traveled" and replace with --travelled--.

Signed and Sealed this  
Twentieth Day of August, 2019

Andrei Iancu  
*Director of the United States Patent and Trademark Office*